(12) United States Patent
Carlton

(10) Patent No.: US 6,843,653 B2
(45) Date of Patent: Jan. 18, 2005

(54) DENTAL IMPLANT

(76) Inventor: Joseph Carlton, 2 Sutton Place Sq., New York, NY (US) 10022-3070

( * ) Notice: Subject to any disclaimer, the term of this patent is extended or adjusted under 35 U.S.C. 154(b) by 0 days.

(21) Appl. No.: 10/162,455

(22) Filed: Jun. 4, 2002

(65) Prior Publication Data
US 2003/0224329 A1 Dec. 4, 2003

(51) Int. Cl.$^7$ ............................................... A61C 8/00
(52) U.S. Cl. ...................................................... 433/174
(58) Field of Search ............................... 433/173, 174, 433/201.1

(56) References Cited

U.S. PATENT DOCUMENTS

| | | | |
|---|---|---|---|
| 2,303,874 A | 12/1942 | Brown | 32/9 |
| 3,618,212 A | 11/1971 | Weissman | 32/10 A |
| 3,732,621 A * | 5/1973 | Bostrom | 433/174 |
| 3,977,081 A | 8/1976 | Zambelli et al. | 32/10 A |
| 3,991,472 A | 11/1976 | Lukesch | 32/9 |
| 4,416,629 A | 11/1983 | Mozsary et al. | 433/174 |
| 4,568,285 A | 2/1986 | Chiaramonte et al. | 433/173 |
| 4,746,293 A | 5/1988 | Lundgren et al. | 433/173 |
| 4,850,869 A | 7/1989 | Steinfort et al. | 433/172 |
| 4,881,897 A | 11/1989 | Franek et al. | 433/169 |
| 4,932,868 A * | 6/1990 | Linkow et al. | 433/174 |
| 5,071,350 A | 12/1991 | Niznick | 433/173 |
| 5,073,110 A | 12/1991 | Barbone | 433/173 |
| 5,092,770 A | 3/1992 | Zakula | 433/172 |
| 5,133,662 A | 7/1992 | Metcalfe | 433/169 |
| 5,211,561 A | 5/1993 | Graub | 433/169 |
| 5,213,502 A * | 5/1993 | Daftary | 433/172 |
| 5,302,125 A | 4/1994 | Kownacki et al. | 433/172 |
| 5,417,570 A | 5/1995 | Zuest et al. | 433/177 |
| 5,480,304 A | 1/1996 | Nardi | 433/172 |
| 5,520,540 A | 5/1996 | Nardi et al. | 433/172 |
| 5,564,922 A * | 10/1996 | Rosa et al. | 433/173 |
| 5,605,457 A | 2/1997 | Bailey et al. | 433/174 |
| 5,662,475 A | 9/1997 | Mena | 433/172 |
| 5,782,918 A | 7/1998 | Klardie et al. | 623/16 |
| 5,839,898 A | 11/1998 | Fernandes | 433/173 |
| 5,842,864 A | 12/1998 | Unger | 433/172 |
| 5,873,720 A * | 2/1999 | Jorneus et al. | 433/172 |
| 5,890,902 A * | 4/1999 | Sapian | 433/173 |
| 5,993,212 A | 11/1999 | Shiner | 433/172 |
| 5,997,299 A * | 12/1999 | Unger | 433/173 |
| 6,102,702 A | 8/2000 | Folsom, Jr. et al. | 433/172 |
| 6,168,436 B1 * | 1/2001 | O'Brien | 433/173 |
| 6,190,169 B1 | 2/2001 | Bluemli et al. | 433/172 |
| 6,287,115 B1 | 9/2001 | Lustig et al. | 433/173 |
| 6,299,447 B1 | 10/2001 | Zuest et al. | 433/172 |
| 6,302,693 B1 | 10/2001 | Mena | 433/172 |
| 2001/0012606 A1 | 8/2001 | Unger | 433/173 |
| 2001/0044095 A1 | 11/2001 | Rizzo et al. | 433/172 |
| 2003/0216735 A1 * | 11/2003 | Altarac et al. | 606/61 |

OTHER PUBLICATIONS

"The Bit one Piece—One Stage™ Implant System", 5 pages.

* cited by examiner

Primary Examiner—Todd E. Manahan
(74) Attorney, Agent, or Firm—Drinker Biddle & Reath LLP

(57) ABSTRACT

A dental implant is provided having an elongated implant body. The implant body includes a first end and a second end. The first end is adapted to be mounted within a patient's mandibular or maxillary bone. An adjustable abutment having a projecting head for receiving a dental prosthesis is moveably mounted in the second end of the implant body. A collar is provided for engaging the second end of the implant body and securing the abutment in a fixed position.

25 Claims, 5 Drawing Sheets

DENTAL IMPLANT

FIELD OF THE INVENTION

The present invention relates to the field of reconstructive dentistry and, more particularly, to dental implants and methods for dental restoration using same.

BACKGROUND OF THE INVENTION

Many people experience natural tooth loss due to disease or injury. Consequently, various techniques have been developed to replace lost teeth. In some cases there are sufficient teeth remaining adjacent the opening where a prosthetic tooth is to be placed, in these cases a bridge may be used. If however, insufficient natural teeth remain to support and stabilize the bridge, a denture may be prepared and seated against the patient's gingiva. In yet other instances, a dental surgeon may use a dental implant.

When a dental implant is to be used, a hole is first drilled into a patient's jawbone (mandibular or maxillary bone), the implant is then attached by either screwing it or tapping it into the opening. After the implant is inserted into the jawbone, the opening in the gingiva is surgically closed and allowed to heal. The healing time is generally up to six months during which time the bone and gingiva will regenerate around the implant to secure it. After sufficient healing time, a second procedure takes place wherein the submerged implant is located and the gingiva is reopened. The dental surgeon attaches an abutment cap to the implant body and another healing period begins.

After the second healing period, the dental surgeon removes the abutment cap and selects an abutment for insertion into the implant body. The prosthetic tooth is positioned on the abutment. In order for the tooth to be properly positioned, the direction of projection of the abutment is often critical. When a number of teeth are to be positioned adjacent one another, it is required that adjacent abutments be substantially parallel. In most cases, when multiple or even single implants are inserted, however, parallelism cannot be achieved. Thus, final installation is almost always achieved by modifying the shape of the abutment head.

Abutments are formed with heads having various angles and lengths so they can properly seat a prosthetic tooth in a patient's mouth. A dental surgeon must estimate and decide which abutment is appropriate for a given situation. This "trial and error" approach creates more work for the dental surgeon by having the dental surgeon repeatedly insert and remove abutments until a proper fit is found. Also, intra-oral connection of components is difficult due to the close tolerances to which the components are made. In addition, the tightening of abutments onto the implant body is difficult due to the shape of the abutment. Also, screws loosen and screws and abutment heads can be swallowed. Furthermore, the abutments may need to be ground to allow the prosthetic tooth to fit properly. Most abutments are made from titanium and, therefore, are more difficult to work with than natural teeth. These procedures are time-consuming and in many cases effect the retention of the prosthetic tooth. Also, in many cases, the final restoration does not fit accurately because the implant has ankylosed with the bone and cannot move.

With the present invention, after the prosthetic appliance is assembled, if there is a tolerance or insertion problem, adjustments may be made.

SUMMARY OF THE INVENTION

The present invention is directed to a dental implant comprising an implant body, an adjustable abutment and a securing collar, which are preferably assembled as one unit. The implant body has a tapered first end and a concave or bowl-shaped second end. The abutment has a convex or rounded end and a projecting head that is adapted to receive a dental prosthesis. The securing collar has an opening that allows it to fit over the abutment. Threads are provided to secure the collar to the implant body.

When using an implant of the present invention, a dental surgeon first makes a hole, through the gingiva, into the patient's mandibular or maxillary bone. He or she then inserts the single component dental implant into the patient's mandibular or maxillary bone, either by screwing it or tapping it into place. After the healing period, the dental surgeon adjusts the abutment to the proper position and secures the abutment in place. Once secured, a dental prosthesis is attached to the abutment. The present invention is contemplated to have a number of advantages over the prior art. First, the abutment is adjustable once the implant is in place. There is no need to remove an abutment head that does not fit to replace it with another that may or may not fit. In addition, there is no need to grind the abutment head or to take an impression to have a new abutment head custom-made.

By using the implant of the present invention, there are fewer steps; namely the re-opening of the gingiva to locate the submerged implant body and affixing of a healing abutment are not required. In addition, there is no need to supply a separate abutment head because of the contemplated single component nature of the invention. Moreover, the possibility of the loss of a component or the swallowing of a component is greatly minimized. This saves the patient and dental surgeon time, effort, discomfort and expense.

BRIEF DESCRIPTION OF THE DRAWINGS

For the purpose of illustrating the invention, the drawings show a form of the invention that is presently preferred. However, it should be understood that this invention is not limited to the precise arrangements and instrumentalities shown in the drawings.

FIG. 3 is a sectional view of a dental implant according to the present invention.

DETAILED DESCRIPTION OF THE DRAWINGS

Figure 1:
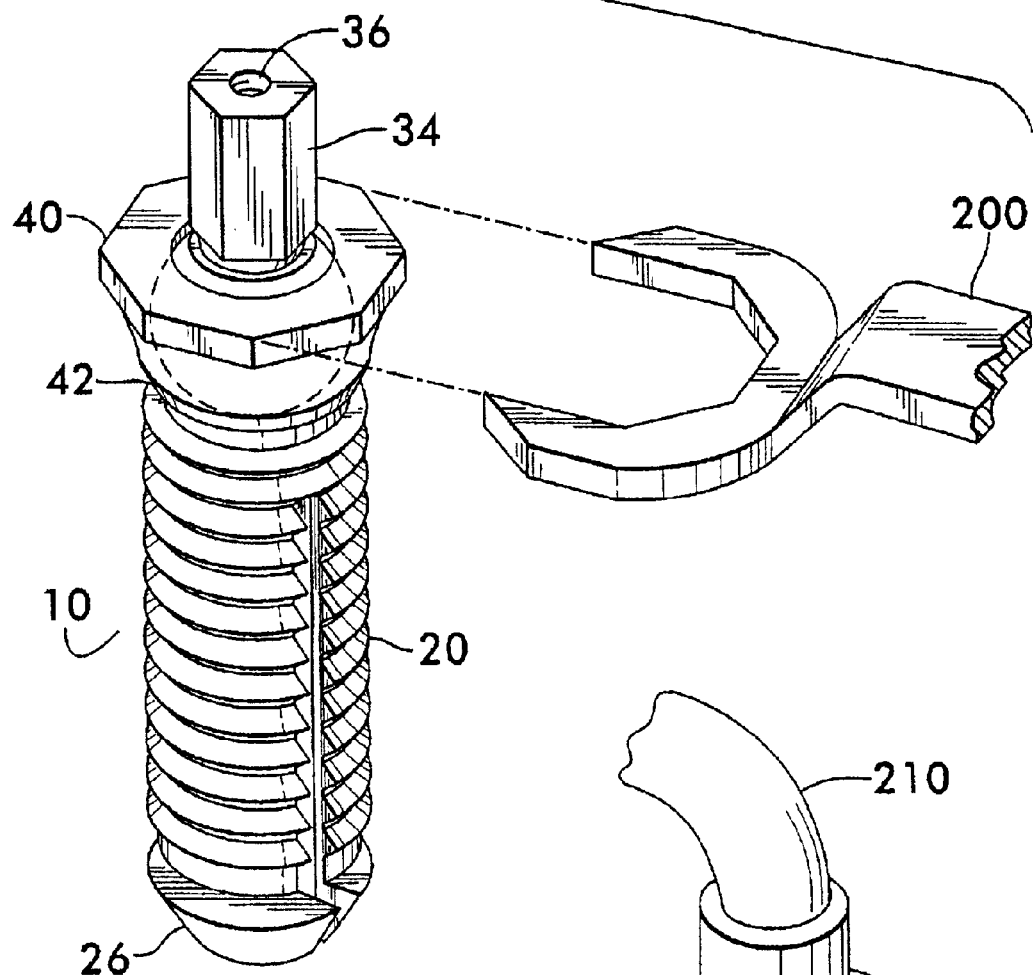
FIG. 1 is a perspective view of a dental implant and tightening key of the present invention.

Referring to the drawings, wherein like numerals indicate like elements, there is shown in FIGS. 1–5 a dental implant that is generally denoted by numeral 10. Implant 10 can be formed from titanium or other suitable materials. The implant 10 generally comprises an implant body 20, an abutment 30 and a securing collar 40 which are constructed in such a way that the securing collar 40 is unable to be removed from the implant body 20. The implant body 20 has an elongated generally cylindrical shape and includes a tapered first end 26, which is to be inserted into an opening in a patient's mandibular or maxillary bone. For this purpose the first end 26 may be provided with external threads (not shown). Opposite the first end 26, the implant body 20 has a concave or bowl-shaped second end 28. Threads 22 are located around the outside periphery of the second end of the implant body 20. An abutment 30 is provided having a convex or spherical portion 32, a projecting head 34 and an aperture 36 in the head. The projecting head 34 preferably has a prismatic shape, having four or more flat surfaces for engagement with a dental prosthesis. The aperture 36 may be threaded to matingly receive a fastener 270 or positioning tool (not shown). The convex portion 32 is adapted to fit into the concave portion 28 of the implant body 20. The securing collar 40 has an opening 46 that is large enough to fit over the abutment head 34.

Figure 4:
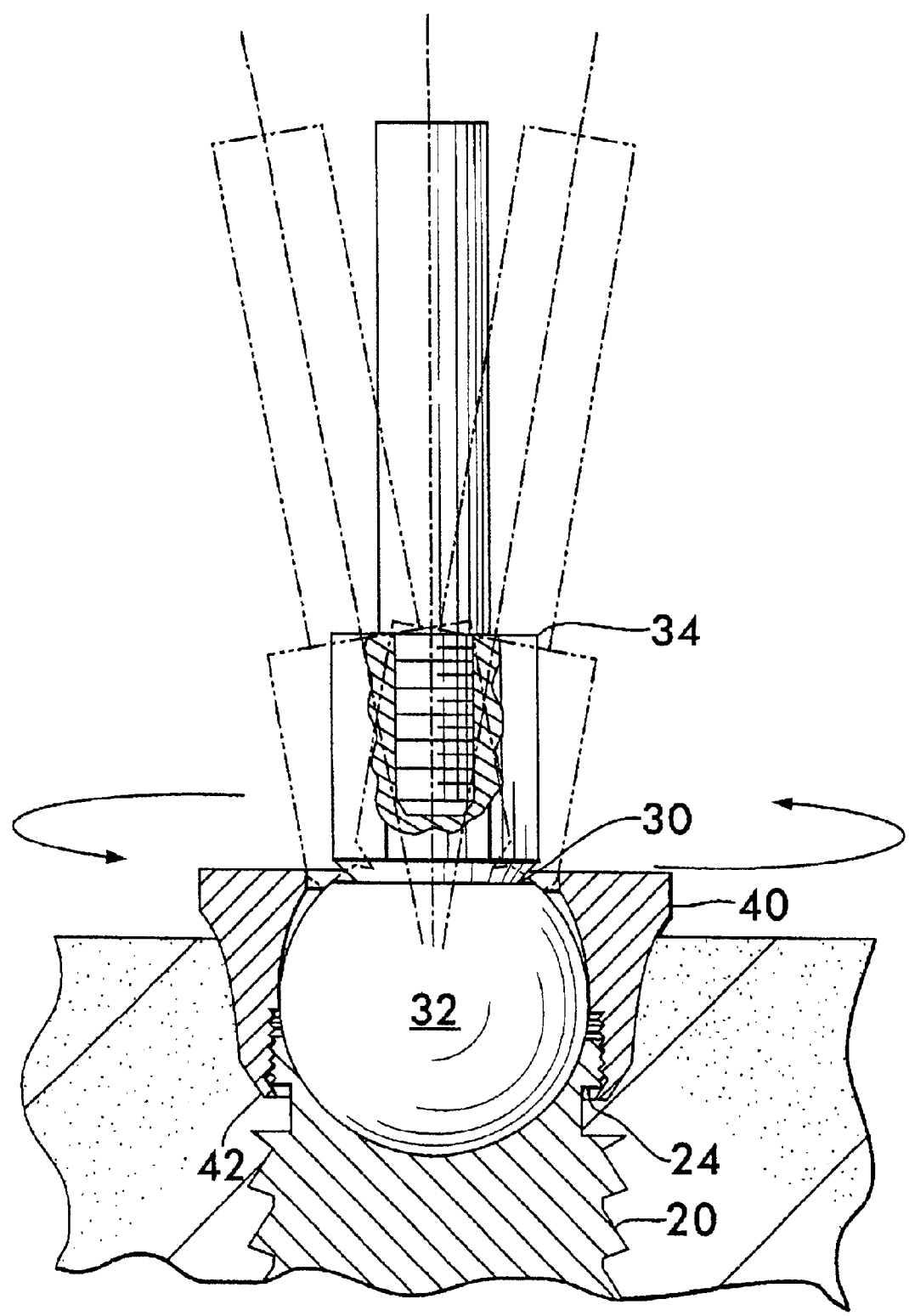
FIG. 4 is a partial sectional view of a dental implant of the present invention depicting movement of the abutment portion thereof.

Collar 40 has internal threads 44 that are adapted to matingly engage the external threads 22 of the implant body 20. The collar 40 may be a threaded sleeve, a locknut, etc. and has a crimped-in or tapered section 42 that is located around the periphery of the end that engages the implant body 20. This crimped-in or tapered section 42 keeps the collar 40 attached to the implant body 20 by engaging a lip 24 when the collar 40 is loosened. As shown in FIG. 4, when the collar 40 is loosened, it is permitted to travel upward along the threads and the abutment is able to rotate and pivot in its socket. The collar or sleeve is limited in its travel as crimped-in or tapered section 42 is unable to travel past the lip 24. (See FIG. 3B.)

Figure 1A:
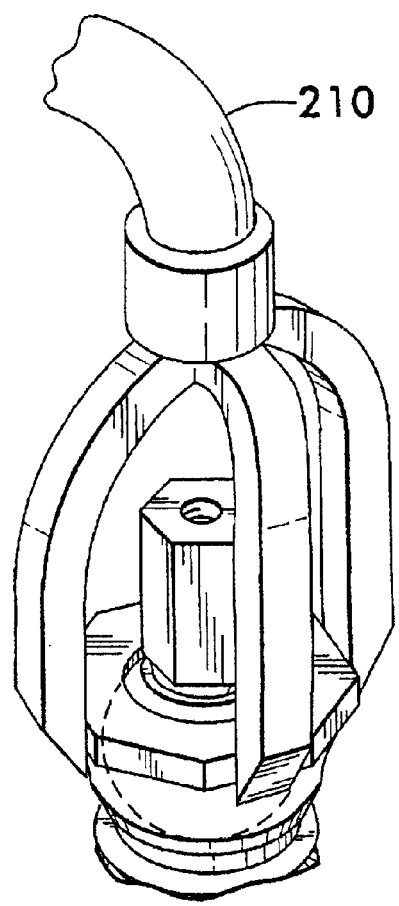
FIG. 1A is an alternative embodiment of the tightening key.
Figure 5:
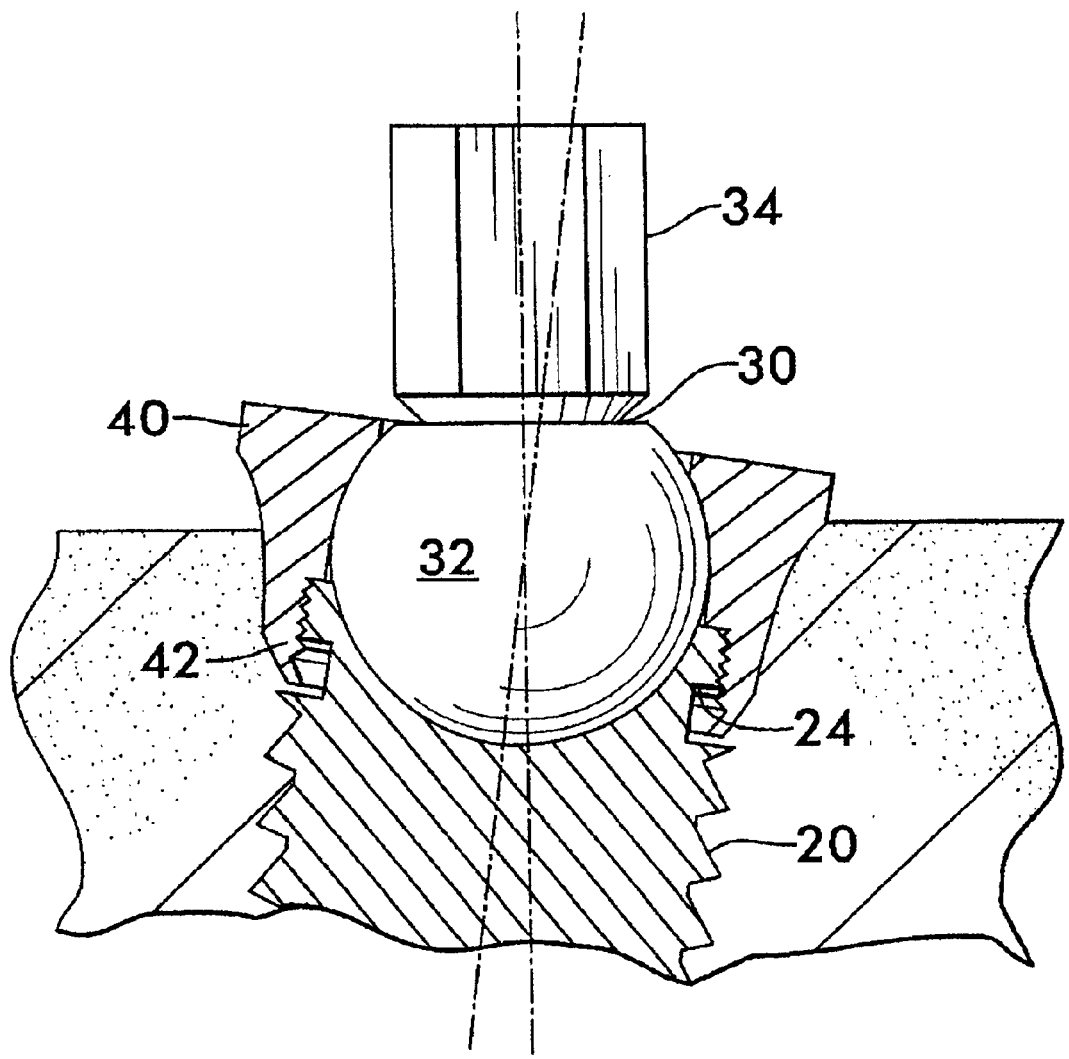
FIG. 5 is a partial sectional view of the dental implant of the present invention depicting the positioning of the abutment portion.

Once an implant 10 has been affixed within a patient's mandibular or maxillary bone 290 and gingiva 280, and the proper healing time has passed, a dental surgeon aligns the abutment 30 to the proper orientation. As shown in FIG. 5, the implant body 20 may not always be inserted perpendicular to the gingiva 280 (due to any number of reasons, such as obstructions, insufficient bone density, etc.). This may require the dental surgeon to adjust the alignment of the abutment. The abutment head 34 may be manually adjusted with a finger to the proper position. The collar may also be secured manually. FIG. 4 shows the potential range of motion once the collar 40 has been loosened upwardly (with the amount of loosening being limited by tapered section 42). A positioning tool (not shown) may be inserted into the aperture 36 of the abutment head 34 to assist in tilting the abutment 30 until the proper projection position has been achieved. The positioning tool can be a simple lever-type implement that is adjusted manually or may be an automated device integrated with a computer for directing the proper alignment. Once alignment is achieved, the dental surgeon tightens the collar 40, using (for example) keys 200, 210 as shown in FIGS. 1 and 1A. Key 200 is used to tighten the collar if sufficient space exists around the implant 10. If there is not sufficient space around the implant 10, key 210 is used to tighten the collar from above.

Figure 2:
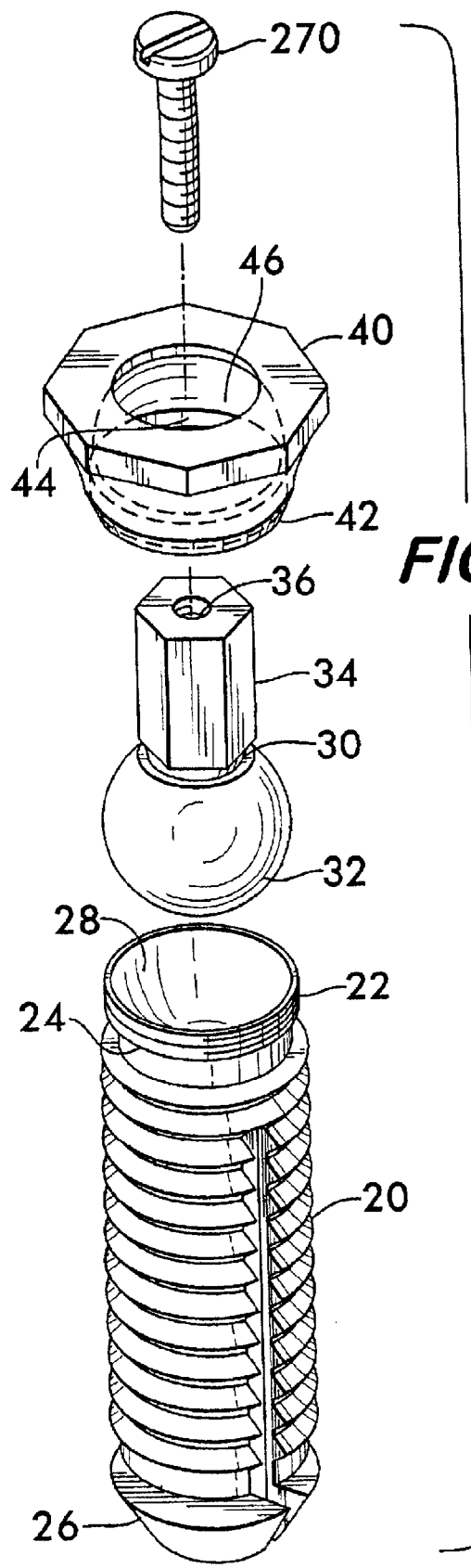
FIG. 2 is an exploded view of the dental implant illustrated in FIG. 1.
Figure 2A:
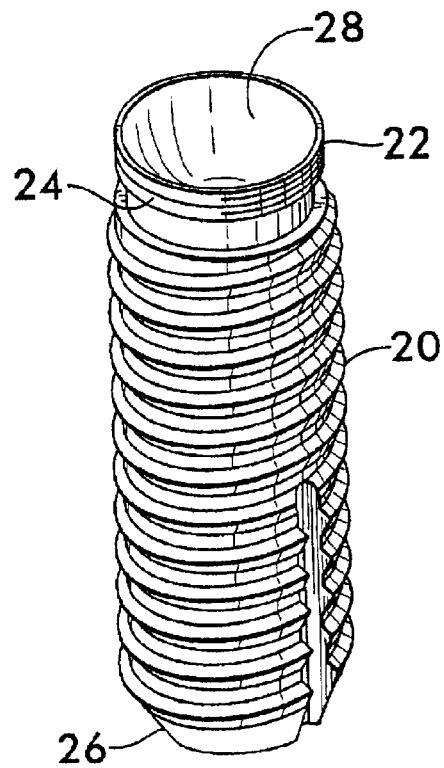
FIG. 2A is an alternative embodiment of the body of the dental implant illustrated in FIG. 1.
Figure 3A:
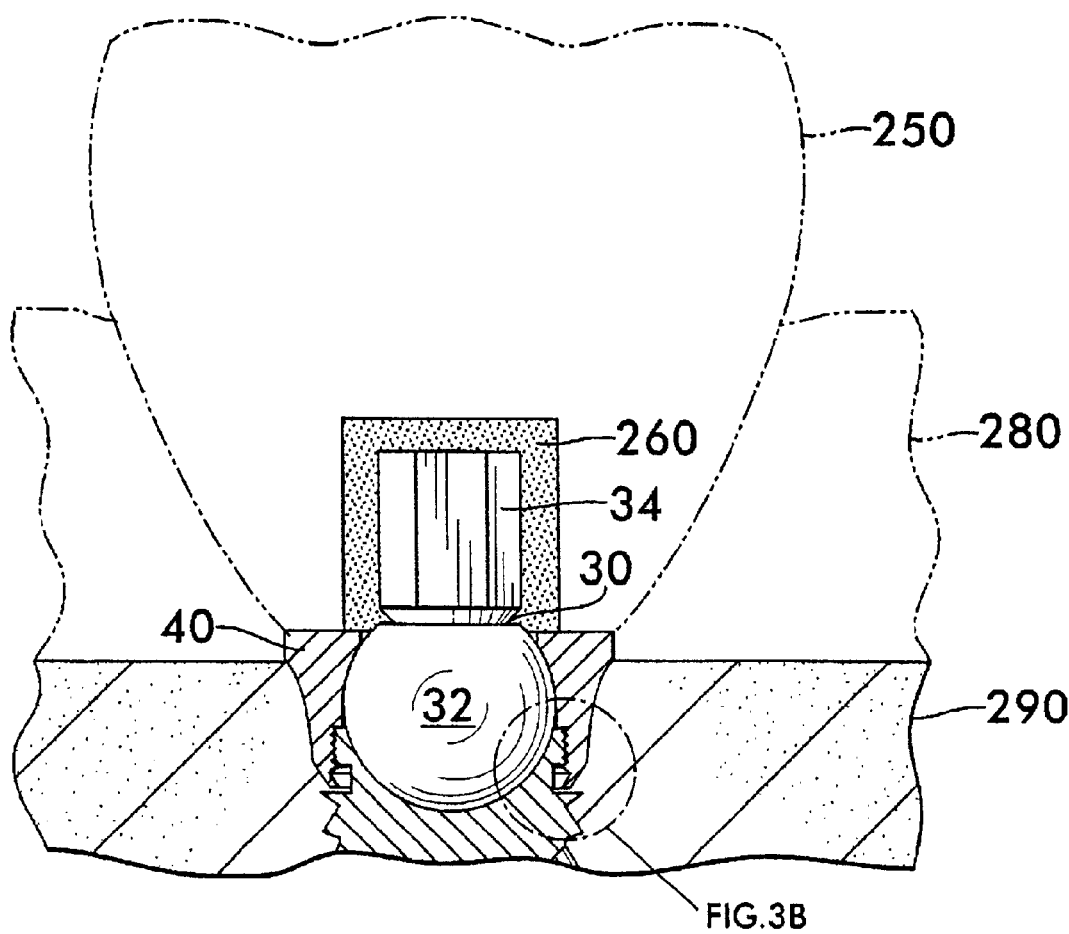
FIG. 3A is a sectional view of the dental implant with a prosthetic tooth (shown in phantom) mounted thereon.
Figure 3B:
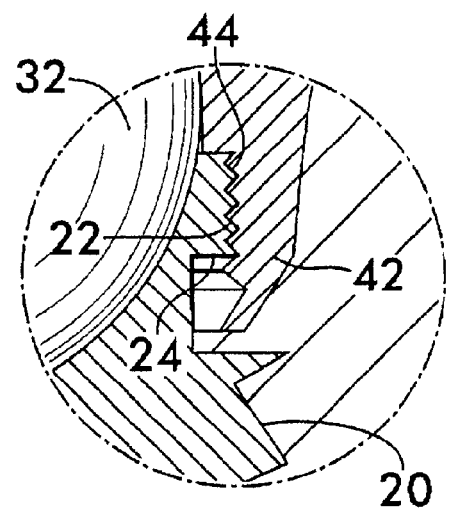
FIG. 3B is a magnified view of a portion of the dental implant, as taken from FIG. 3A.

With the abutment 30 secured, the dental surgeon may now attach the dental prosthesis 250 to the abutment head 34. A fastener 270, to attach the prosthetic tooth 250, to the abutment head 34. The fastener 270, as shown in FIGS. 2 and 3, may be a threaded screw. A bolt, expanding screw, dowel, pin, rivet or any other suitable fastener may also be used. Alternatively, as shown in FIG. 3A, an adhesive 260 may be used to affix the prosthesis 250 to the abutment head 34. Appropriate adhesives include cement, glue, epoxy, etc.

Although the invention has been described and illustrated with respect to exemplary embodiments thereof, it should be understood by those skilled in the art that the foregoing and various other changes, omissions and additions may be made therein and thereto, without parting from the spirit and scope of the present invention.

What is claimed is:

1. A dental implant for mounting and supporting a dental prosthesis, the implant comprising:

a. an elongated implant body having a first end and a second end, the first end adapted to be mounted within a patient's mandibular or maxillary bone;

b. an abutment, having a projecting head at one end for receiving a dental prosthesis, the abutment also having a substantially round mounting end which is adapted for adjustable engagement within the second end of the implant body; and c. a collar for engaging the second end of the implant body and securing the abutment in a fixed position against the implant body, the collar comprising an engagement surface for direct engagement with a bottom portion of the dental prosthesis, wherein forces exerted on the dental prosthesis substantially are transferred to the engagement surface of the collar.

2. The dental implant of claim 1, wherein the implant body further comprises external threads around the first end to mount the implant body within the mandibular or maxillary bone.

3. The dental implant of claim 1, wherein the implant body is tapered toward the first end.

4. The dental implant of claim 1, wherein the implant body further comprises external threads around the periphery of the second end to matingly engage a corresponding set of internal threads on the collar.

5. The dental implant of claim 4, wherein the implant body further comprises a slot adjacent the threads on the second end, the slot defining an axially positioned top boundary and a bottom boundary around the outside surface of the second end.

6. The dental implant of claim 5, wherein the collar comprises a tapered section positioned around the outer periphery of the end having the internal threads, the tapered section of the collar engaging the boundaries of the slot in the implant body to limit the axial movement of the collar once threaded on the second end of the implant body.

7. The dental implant of claim 1, wherein the abutment further comprises an aperture adapted for receipt of a tool for adjusting the position of the abutment against the implant body.

8. The dental implant of claim 1, wherein the mounting end of the abutment has a convex surface, and the second end of the implant body has a corresponding concave surface for receipt of the abutment.

9. The dental implant of claim 1, wherein the projecting head has a hexagonal configuration.

10. The dental implant of claim 1, further comprising a fastener for securing a dental prosthesis to the abutment.

11. The dental implant of claim 1 wherein the implant is formed from titanium.

12. A dental implant for mounting and supporting a dental prosthesis, the implant comprising:

a. an elongated implant body having a first end and a second end, the first end adapted to be mounted within a patient's mandibular or maxillary bone;

b. an abutment, having a projecting head at one end for receiving a dental prosthesis, the abutment also having a mounting end which is adapted for adjustable engagement within the second end of the implant body;

c. a collar for engaging the second end of the implant body and securing the abutment in a fixed position against the implant body;

d. the implant body further comprising external threads around the periphery of the second end to matingly engage a corresponding set of internal threads on the collar and a slot adjacent the threads on the second end, the slot defining an axially positioned top boundary and a bottom boundary around the outside surface of the second end; and e. the collar further comprising a tapered section positioned around the outer periphery of the end having the internal threads, the tapered section of the collar engaging the boundaries of the slot in the implant body to limit the axial movement of the collar once threaded on the second end of the implant body;

f. wherein once the collar is engaged with the second end of the implant body, the tapered section is unable to travel past the top boundary of the second end.

13. The dental implant of claim 12, wherein the collar has an engagement surface for receipt of a key for causing rotation of the collar onto the threads of the implant.

14. The dental implant of claim 13, wherein the periphery of the engagement surface has an octagonal configuration.

15. A dental implant comprising:

a. an implant body for inserting into a patient's mandibular or maxillary bone;

b. tiltable, rotatable abutment for positioning a dental prosthesis, the abutment adapted to be adjustably positioned within one end of the implant body; and c. a locking member to secure and fix the position of the abutment within the implant body, the locking member comprising a top portion with a surface for directly engaging a bottom portion of the dental prosthesis.

16. The dental implant of claim 15, wherein the locking member has a crimping section around its periphery and the implant body has a slot around its periphery, the crimping section engaging the slot to prevent removal of the locking member from said implant body when the locking member is loosened.

17. The dental implant of claim 15, wherein the abutment has a rounded ball shaped end and a head on the opposite end, the ball shaped end being adapted to fit with a mating socket on the implant body while allowing tilt and rotation.

18. The dental implant of claim 15, wherein the implant body has helical threads around its outside surface.

19. The dental implant of claim 15, wherein the abutment has a hexagonal-shaped head, the hexagonal-shaped section further comprising an aperture for receipt of a positioning tool.

20. A dental implant comprising:

a. an implant body for inserting into a patient's mandibular or maxillary bone;

b. a tiltable, rotatable abutment for positioning a dental prosthesis, the abutment adapted to be adjustably positioned within one end of the implant body; and c. a locking member to secure and fix the position of the abutment within the implant body;

d. wherein the locking member has a crimping section around its periphery and the implant body has a slot around its periphery, the crimping section engaging the slot to prevent removal of the locking member from said implant body when the locking member is loosened.

21. A one piece dental implant for mounting and supporting a dental prosthesis, the implant comprising:

a. an elongated implant body having a first end and a second end, the first end adapted to be mounted within a patient's mandibular or maxillary bone;

b. an abutment, having a projecting head at one end for receiving a dental prosthesis, the abutment also having a substantially ball shaped mounting end which is adapted for adjustable engagement within the second end of the implant body; and c. an adjustable collar engaging the second end of the implant body, adjustment of the collar in one position securing the abutment in a fixed position with respect to the implant body and in a second position permitting the abutment to move with respect to the implant body to reset the position of the projecting head, the collar comprising a substantially flat surface for engaging a bottom portion of the dental prosthesis, wherein forces exerted on the dental prosthesis are transferred to the collar.

22. The dental implant of claim 21, wherein the engagement of the implant body with the collar is created by an external threaded surface around the periphery of the second end and a corresponding set of internal threads on the collar.

23. The dental implant of claim 22, wherein the implant body further comprises a slot formed adjacent the threads on the second end, the slot defining an axially positioned top boundary and a bottom boundary around the outside surface of the second end; and wherein the collar comprises a tapered portion that fits within the boundaries of the slot in the implant body, the projection of the tapered portion limiting the axial movement of the collar by engagement with the slot boundaries during adjustment of the abutment.

24. A dental implant comprising:

a. an implant body comprising a first end and a second end, threads on the second end for engaging a collar, a slot adjacent the threads on the second end, the slot defining an axially positioned top boundary and a bottom boundary around the outside surface of the second end, and b. the collar comprising a first end and a second end, the second end of the collar having internal threads, a tapered section positioned around the outer periphery of the second end, the tapered section of the collar alternately engaging the top and bottom boundaries of the slot in the implant body to limit the axial movement of the collar once threaded on the second end of the implant body such that the collar is not removeable from the implant body.

25. A one piece dental implant for mounting and supporting a dental prosthesis, the implant comprising:

a. an elongated implant body having a first end and a second end, the first end adapted to be mounted within a patient's mandibular or maxillary bone;

b. an abutment, having a projecting head at one end for receiving a dental prosthesis, the abutment also having a mounting end which is adapted for adjustable engagement within the second end of the implant body; and c. an adjustable collar engaging the second end of the implant body, adjustment of the collar in one position securing the abutment in a fixed position with respect to the implant body and in a second position permitting the abutment to move with respect to the implant body to reset the position of the projecting head;

d. wherein the engagement of the implant body with the collar is created by an external threaded surface around the periphery of the second end and a corresponding set of internal threads on the collar and e. wherein the implant body further comprises a slot formed adjacent the threads on the second end, the slot defining an axially positioned top boundary and a bottom boundary around the outside surface of the second end; and f. wherein the collar comprises a tapered portion that fits within the boundaries of the slot in the implant body, the projection of the tapered portion limiting the axial movement of the collar by engagement with the slot boundaries during adjustment of the abutment such that the collar is not removable from the implant body.

* * * * *